(12) United States Patent
Curtis

(10) Patent No.: US 11,565,113 B2
(45) Date of Patent: Jan. 31, 2023

(54) METHOD FOR STIMULATING HEART MUSCLE ACTIVITY DURING THE REFRACTORY PERIOD

(71) Applicant: Guy P. Curtis, San Diego, CA (US)

(72) Inventor: Guy P. Curtis, San Diego, CA (US)

(73) Assignee: GUY P. CURTIS AND FRANCES L. CURTIS TRUST, San Diego, CA (US)

( * ) Notice: Subject to any disclaimer, the term of this patent is extended or adjusted under 35 U.S.C. 154(b) by 380 days.

(21) Appl. No.: 16/653,538

(22) Filed: Oct. 15, 2019

(65) Prior Publication Data

US 2020/0038661 A1 Feb. 6, 2020
US 2020/0398056 A9 Dec. 24, 2020

Related U.S. Application Data

(62) Division of application No. 14/695,237, filed on Apr. 24, 2015, now abandoned.

(51) Int. Cl.
*A61N 1/36* (2006.01)
*A61N 1/05* (2006.01)
*A61N 1/365* (2006.01)

(52) U.S. Cl.
CPC ........ *A61N 1/36114* (2013.01); *A61N 1/0587* (2013.01); *A61N 1/36507* (2013.01)

(58) Field of Classification Search
CPC .............. A61N 1/36114; A61N 1/0587; A61N 1/36507
See application file for complete search history.

(56) References Cited

U.S. PATENT DOCUMENTS

2008/0132966 A1* 6/2008 Levin ................. A61N 1/36114 607/119
2011/0301666 A1* 12/2011 Curtis ................ A61N 1/36114 607/59

* cited by examiner

*Primary Examiner* — Mallika D Fairchild

(57) ABSTRACT

A system and method for improving heart contractions during a heart function cycle (heartbeat) of a patient requires detecting a local electrical event (depolarization) during the cycle. This local electrical event is then used to trigger a stimulation interval $\Delta t$ at a time $t_0$. Importantly, the stimulation interval $\Delta t$ is set to end at a time $t_1$ during the absolute refractory period of the heart function cycle. At the time $t_1$, a stimulator is triggered to stimulate a local sympathetic nerve on the epicardial surface of the heart. With this stimulation the sympathetic nerve secretes norepinephrine to improve a subsequent contraction of the heart.

13 Claims, 2 Drawing Sheets

METHOD FOR STIMULATING HEART MUSCLE ACTIVITY DURING THE REFRACTORY PERIOD

This application is a divisional of application Ser. No. 14/695,237, filed Apr. 24, 2015. The contents of application Ser. No. 14/695,237 are incorporated herein by reference.

FIELD OF THE INVENTION

The present invention pertains to systems and methods for improving heart muscle function. More particularly, the present invention pertains to systems and methods which stimulate sympathetic nerves to secrete norepinephrine during the absolute refractory period of a heart muscle cycle, to thereby improve heart muscle contraction. The present invention is particularly, but not exclusively, useful as a system or method wherein nerve stimulation in the absolute refractory period is triggered by a local electrical depolarization of the heart muscle.

BACKGROUND OF THE INVENTION

A normal heart muscle cycle (i.e. a heartbeat) is repetitive and is characterized by several well-known and distinctly identifiable mechanical and electrical characteristics. In its mechanical cycle, the heart muscle alternately functions to pump blood into the vasculature of a patient by its contractions (systole), and to receive blood from the vasculature by its relaxation (diastole). Physiologically, the heart muscle cycle is the result of an electrical cycle that is superposed on the mechanical cycle. Of immediate interest here, however, is the absolute refractory period.

During the absolute refractory period, which follows cell firing during diastole, and which is approximately 120-300 msec in duration, the heart muscle is not able to respond to an electrical stimulation. Sympathetic nerves on the epicardial surface of the heart, however, can be electrically stimulated during the absolute refractory period to thereby secrete norepinephrine. The import here is that the secreted norepinephrine can then subsequently assist in controlling and improving a heart muscle contraction. It is, of course, essential to stimulate the sympathetic nerve during the heart's absolute refractory period so that the electrical and mechanical cycles of the heart are not disturbed.

Identifying the appropriate time for electrically stimulating a sympathetic nerve must necessarily be established relative to the heart muscle cycle. Heretofore, the timing for nerve stimulation has been determined by the operation of a pacing device. For example, U.S. Pat. No. 8,463,376, which issued to Curtis for an invention entitled "System and Method for Transvascular. Activation of Cardiac Nerves with Automatic Restart," discloses and claims the electrically paced stimulation of a heart muscle.

The present invention now recognizes that the heart muscle itself creates natural signals (i.e. electrical events) which can be used to trigger a subsequent electrical stimulation of a sympathetic nerve. Importantly, this subsequent nerve stimulation can be timed to occur in the absolute refractory period of the heart muscle cycle.

With the above in mind, it is an object of the present invention to provide a system and method for electrically stimulating a sympathetic nerve of a patient in response to a naturally occurring electrical event of the heart muscle. Another object of the present invention is to electrically stimulate a sympathetic nerve of a patient using a single pulse, or multiple pulses, during the absolute refractory period of a heart muscle cycle to assist with a contraction of the patient's heart muscle. Still another object of the present invention is to provide a system and method for electrically stimulating a sympathetic nerve of a patient which is easy to use, is simple to manufacture and is commercially cost effective.

SUMMARY OF THE INVENTION

In accordance with the present invention, a system and method are provided to improve the heart contractions of a patient during a heart function cycle (heartbeat). To set up the system for its operation, a deployment catheter is used to position an electrode and a sensor in an epicardial vein that is located on the epicardial surface of the heart, A proper positioning of the electrode and the sensor requires they be located adjacent a sympathetic nerve.

In an overview of the present invention, it is to be appreciated that, during each heart function cycle, the present invention detects a local electrical event (depolarization) of the heart muscle. Based on the occurrence of this local electrical event at a time $t_0$, a stimulation interval, $\Delta t$, is established. In detail, $\Delta t$ begins at the time $t_0$, and it ends at a time $t_1$ during the absolute refractory period of the heart function cycle. At the time $t_1$, the sympathetic nerve, which is located on the epicardial surface of the heart, is stimulated. With this stimulation the sympathetic nerve will secrete norepinephrine to improve a subsequent contraction of the heart.

Structurally, a device of the present invention includes a sensor for detecting the local electrical event of the heart, at the time to. Typically, a local electrical event is selected and used that occurs during a heart contraction, during diastole, in the patient's natural heart muscle cycle. The device also includes a timer that is activated at the time $t_0$ and is used for measuring the predetermined stimulation interval $\Delta t$. Recall, $\Delta t$ extends between the start time $t_0$ and the time $t_1$ in the absolute refractory period of the patient's heart cycle ($\Delta t = t_1 - t_0$). Further, the device includes a stimulator that is connected with an electrode for stimulating the sympathetic nerve with at least one electrical pulse at the time $t_1$. Preferably, the electrical pulse(s) for stimulating the sympathetic nerve has(have) a predetermined intensity that is essentially less than about three times the intensity required for activating a contraction of the heart muscle.

For an alternate embodiment of the present invention, the system of the present invention may also include a pacing device which, along with the sensor, can be selectively connected by a switch with the stimulator. For this embodiment, when selected, the pacing device is used to electronically establish $t_0$. Although the switch can be used to selectively alternate between a connection of the stimulator with the sensor, or with the pacing device, the overall purpose and functionality of the system remains unchanged.

Additional components for the device of the present invention include a voltage source that will generate the electrical pulse at the time $t_1$. These components also include a computer for coordinating an operation of the stimulator with respective operations of the sensor, the pacing device, the switch, and the timer.

From a functional perspective, the methodology of the present invention is dependent on the heart function cycle. Accordingly, a method for electrically stimulating a sympathetic nerve of a patient to improve heart function requires first positioning an electrode/sensor in an epicardial vein, on the epicardial surface of the heart, adjacent the sympathetic nerve. The electrode/sensor is then used to detect a local electrical event. Specifically, the local electrical event that is to be detected by the sensor needs to occur near the electrode and will result from the patient's natural heart muscle cycle.

Once a local electrical event is detected, a computer can then be used to establish a predetermined stimulation interval $\Delta t$ that will extend from the start time $t_0$, to a time $t_1$. As noted above, the time $t_1$ needs to fall in the absolute refractory period of the patient's natural heart muscle cycle ($t_1 - t_0 = \Delta t$). The computer can then activate the stimulator at the time $t_1$. The purpose here, of course, is to electrically stimulate the sympathetic nerve with at least one electrical pulse, to thereby improve a subsequent contraction of the patient's heart muscle.

With the above in mind, it is to be understood that an operation of the present invention requires consecutively repeating the stimulation interval $\Delta t$ for each heart function cycle. Also, the stimulation interval $\Delta t$ that determines when a sympathetic nerve is to be stimulated is in an approximate range of 100-120 msec. Further, the electrical pulse(s) for stimulating the sympathetic nerve has(have) a predetermined intensity that is less than about three times the intensity required for activating a contraction of the heart muscle.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF THE PREFERRED EMBODIMENTS

Figure 1:
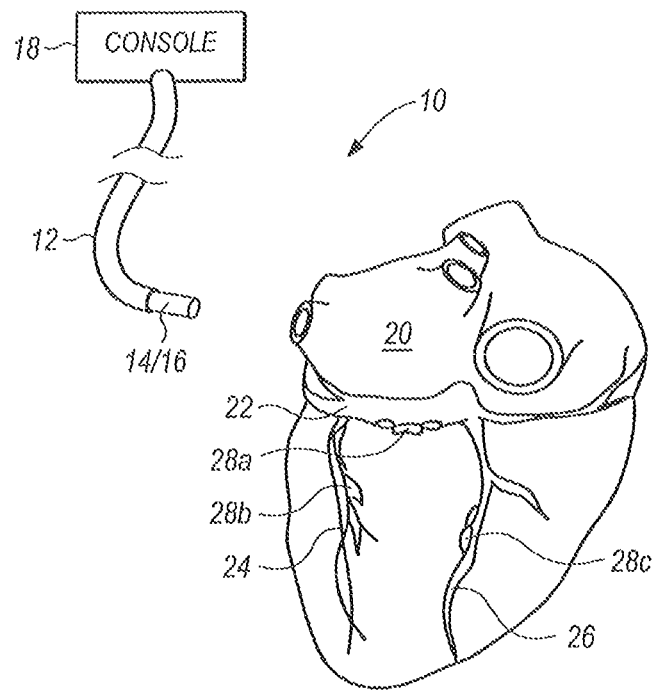
FIG. 1 is a depiction of a system in accordance with the present invention shown together with the intended environment of its operation.

Referring initially to FIG. 1, a system for electrically stimulating a sympathetic nerve of a patient to improve heart function is shown and is generally designated 10. As shown, the system 10 includes a deployment catheter 12 which has a sensor 14 and an electrode 16 that are mounted in combination at the distal end of the deployment catheter 12. In addition to the mechanical components mentioned above, the system 10 also includes various electronic components which are disclosed below with reference to FIG. 2. As disclosed below, these electronic components are mounted in the console 18 and interact with each other to provide operational control over the system 10. For purposes of the present invention, it is to be appreciated that the console 18 may be either extracorporeal or implantable. For example, as an implantable, the console 18 may be part of a pacemaker or a defibrillator.

Still referring to FIG. 1, a heart muscle 20 is shown as the surgical target for the present invention. Anatomically, a view of the diaphragmatic surface of the heart muscle 20 shows its coronary sinus 22 and several connecting veins. In particular, the posterior vein 24 of the left ventricle, and the middle cardiac vein 26 are shown. Also shown are sympathetic nerve(s) 28 in the nervous system, of which the nerve bundles 28a, 28b and 28c are only exemplary. Importantly, the nerves 28 are located on the epicardial surface of the left ventricle, and they are adjacent to either the coronary sinus 22 or one of the veins connected with the coronary sinus 22 (e.g. veins 24 or 26).

Figure 2:
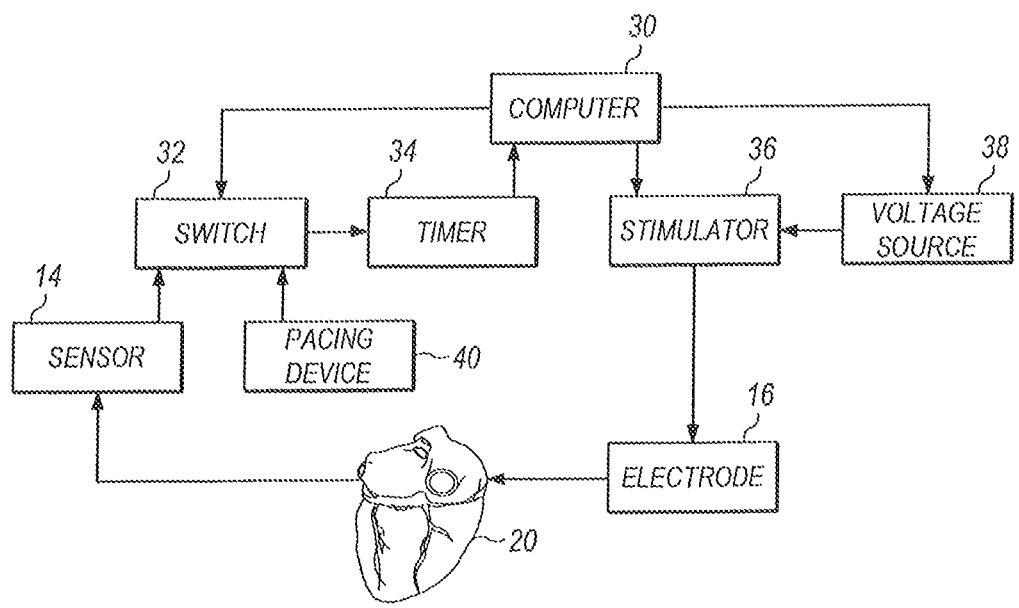
FIG. 2 is a functional layout of the components employed in a system of the present invention.

Referring now to FIG. 2, it will be seen that a computer 30 is provided for the system 10, and that the computer 30 is electronically connected with a switch 32, a timer 34, a stimulator 36 and a voltage source 38. Optionally, a pacing device 40 can also be electronically incorporated with the aforementioned components. As will be best appreciated by cross-reference between FIG. 1 and FIG. 2, the switch 32, the timer 34, the stimulator 36, and the voltage source 38, as well as the pacing device 40, can all be mounted on the extracorporeal console 18. On the other hand, as disclosed above, the sensor 14 and the electrode 16 are incorporated into the deployment catheter 12.

For a disclosure of their interaction with each other, the components mentioned above are shown in FIG. 2 in their relationship with the heart muscle 20. Specifically, the sensor 14 and the electrode 16 are operationally shown in direct contact with the heart muscle 20. Depending on whether the operation of system 10 is to rely on a paced event, which can be alternatively provided using the pacing device 40, the switch 32 is used to alternatively connect the sensor 14 or the pacing device 40 with the timer 34. Further, under the control of the computer 30, the stimulator 36 is energized by the voltage source 38 for a timed activation of the electrode 16. In turn, the electrode 16 will stimulate a sympathetic nerve 28 on the heart muscle 20. As envisioned for the present invention, each pulse that is used to stimulate the sympathetic nerve 28 will have an intensity that is less than about three times the intensity required for activating a contraction of the heart muscle 20.

Figure 3:
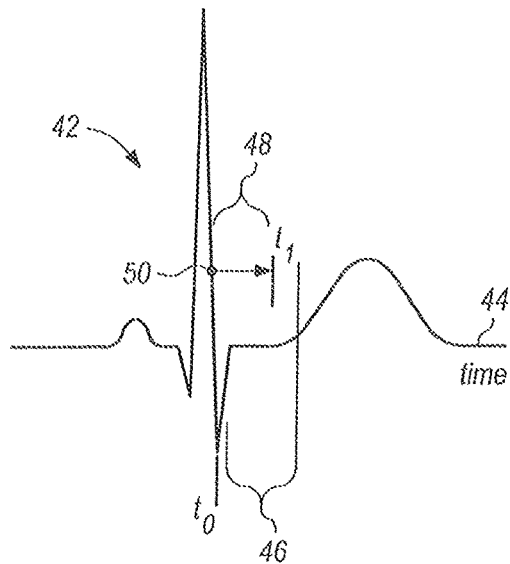
FIG. 3 is a time-line depiction of a heart muscle cycle with an operation of the present invention superposed thereon in its relation to the absolute refractory period.

The depiction of a normal heart function cycle (i.e. a heartbeat) is shown in FIG. 3 and is generally designated 42. As shown, the heart function cycle 42 is depicted by an isoelectric line 44. In this context, the absolute refractory period 46 of the heart function cycle 42 is shown in its overall relationship with the heart function cycle 42. As discussed above, the absolute refractory period 46 is a period of time in which the heart muscle 20 is not able to respond to an electrical stimulation. As also discussed above, the present invention requires there be a stimulation of a sympathetic nerve 28 during the absolute refractory period 46. To do this, the system 10 of the present invention establishes a stimulation interval 48 that will begin with an electrical event 50 at a time $t_0$ and will end at a time $t_1$ in the absolute refractory period 46 when a sympathetic nerve 28 is stimulated.

Still referring to FIG. 3 an exemplary electrical event 50 is shown on the isoelectric line 44 to occur at a time $t_0$. As envisioned by the present invention, the exact time for selection of an occurrence for the electrical event 50 is somewhat arbitrary. Preferably, however, it will be before and relatively near the beginning of the absolute refractory period 46. As indicated above, in an alternate embodiment of the present invention a pacing device 40 can be employed to set the start time $t_0$. In any event, once a time $t_0$ has been determined for the electrical event 50, or set by the pacing device 40, the stimulation interval 48 can be established. Mathematically expressed, $t_1 - t_0 = \Delta t$, wherein $\Delta t$ is the stimulation interval 48. Preferably, $\Delta t$ will be in an approximate range of 100 to 120 msec. Again, note with reference to FIG. 3 that the time $t_1$ falls within the absolute refractory period 46.

Figure 4:
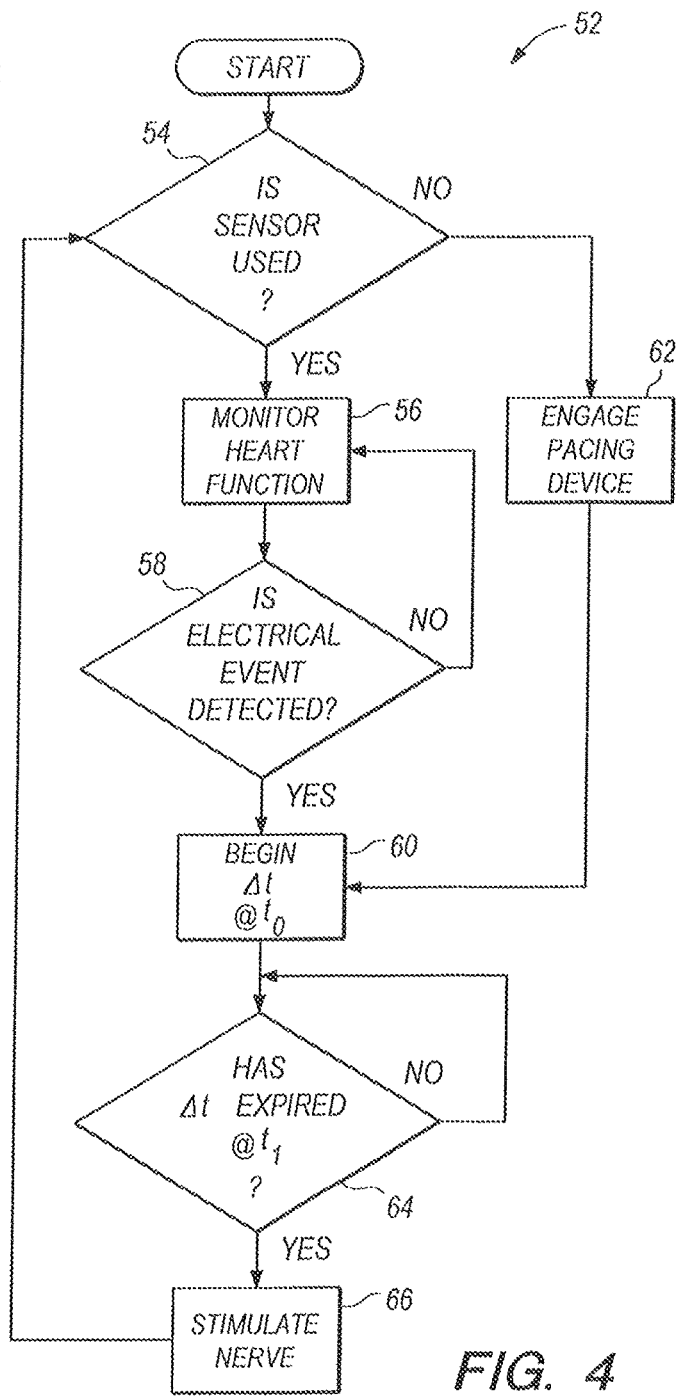
FIG. 4 is a logic flow chart for the functional tasks that are required during an operation of the computer-controlled system of the present invention.

A logic flow chart for the tasks to be performed during an operation of the present invention is shown in FIG. 4 and is generally designated 52. After the start of an operation, the inquiry block 54 questions whether the sensor 14 is being used. If so, task block 56 requires that the heart muscle function be monitored by the sensor 14. Next, inquiry block 58 asks whether an electrical event 50 has been detected. If not, the sensor 14 continues monitoring the heart function cycle 42. On the other hand, if an electrical event 50 is detected, task block 60 requires the establishment of a stimulation interval 48. As disclosed above, the stimulation interval Δt 48 extends from a time $t_0$ when the electrical event 50 is detected, to a time $t_1$ when a pulse(s) is(are) to be fired by the stimulator 36 to stimulate a sympathetic nerve 28. Recall, in an alternate embodiment of the present invention, a pacing device 40, rather than the sensor 14, is used to trigger the stimulation interval 48. Thus, for the alternate embodiment, inquiry block 54 together with task block 62 directs there be an engagement of the timer 34 with the pacing device 40. In all embodiments, however, the inquiry block 64 and task block 66, together, indicate that when the stimulation interval 48 has expired, the stimulator 36 is activated by the computer 30 to stimulate the sympathetic nerve 28. The system 10 then proceeds to monitor the next heart function cycle 42.

While the particular Method for Stimulating Heart Muscle Activity During the Refractory Period as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A method for electrically stimulating a sympathetic nerve of a patient with at least one electrical pulse to improve heart function, the method comprising the steps of:
    pre-programming each electrical pulse with an intensity having a magnitude and a duration, wherein the magnitude is as much as but less than three times a threshold value that would otherwise directly stimulate the heart muscle;
    positioning an electrode/sensor in an epicardial vein, on the epicardial surface of the heart adjacent the sympathetic nerve;
    using a pacing device to detect a local electrical event at a distance from the electrode/sensor to trigger a start time to for a predetermined stimulation interval;
    waiting a predetermined time interval Δt after the start time to, until a time $t_1$, wherein $t_1$ is in the absolute refractory period of the patient's natural heart muscle cycle ($t_1-t_0=\Delta t$;
    activating a stimulator at the time $t_1$ to electrically stimulate the sympathetic nerve with at least one electrical pulse from the electrode/sensor for a release of norepinephrine during the absolute refractory period; and
    controlling the pre-programmed intensity of each pulse during the activating step to indirectly assist a subsequent natural stimulation of the heart muscle for improved contractions of the heart muscle after the absolute refractory period.

2. The method as recited in claim 1 wherein Δt constitutes the stimulation interval, and the method further comprises the step of consecutively repeating the stimulation interval.

3. The method as recited in claim 1 wherein Δt is in a range of 100-120 msec.

4. A method for electronically stimulating a sympathetic nerve of a patient with at least one electrical pulse to improve heart muscle function, the method comprising the steps of:
    pre-programming each electrical pulse with an intensity having a magnitude and a duration wherein, the magnitude is as much as but less than three times a threshold value that would otherwise directly stimulate the heart muscle;
    positioning an electrode/sensor in an epicardial vein adjacent the sympathetic nerve, wherein the sympathetic nerve is located on the epicardial surface over the left ventricle of the heart muscle;
    using a pacing device to trigger a start time $t_0$ for a stimulation interval, wherein $t_0$ is selected from the group consisting of a local event detected by the pacing device and a time $t_0$ established by the pacing device;
    stimulating the sympathetic nerve at the end of the stimulation interval with at least one electrical pulse from the electrode/sensor during the absolute refractory period in the heart muscle cycle to secrete norepinephrine from the sympathetic nerve;
    controlling the pre-programmed intensity of each pulse during the stimulating step to indirectly assist a subsequent natural stimulation of the heart muscle for improved contractions of the heart muscle after the absolute refractory period; and
    repeating the stimulating step during each successive heart function cycle.

5. The method as recited in claim 4 further comprising the steps of:
    pacing a sequence of stimulation intervals with the pacing device; and
    coordinating the stimulating step with the pacing step to stimulate the sympathetic nerve.

6. The method as recited in claim 5 comprising the step of engaging the pacing device with a timer $t_0$ establish a stimulation interval Δt, wherein the stimulation interval Δt begins at a start time $t_0$ and ends at a time $t_1$.

7. The method as recited in claim 6 wherein the time $t_1$ is in the absolute refractory period of the heart muscle function cycle.

8. The method as recited in claim 6 wherein $t_0$ is outside the absolute refractory period.

9. The method as recited in claim 6 wherein the stimulating step is accomplished at the time $t_1$.

10. The method as recited in claim 7 wherein the start time $t_0$ is triggered by a local electrical event in the patient's heart muscle during diastole of the heart muscle.

11. The method as recited in claim 9 wherein Δt is in a range of 100-120 msec.

12. The method as recited in claim 11 wherein the electrical pulse for stimulating the sympathetic nerve has a predetermined intensity less than three times the intensity required for activating a contraction of the heart muscle.

13. A method for electronically stimulating a sympathetic nerve of a patient with at least one electrical pulse to improve heart muscle function, the method comprising the steps of:
    pre-programming each electrical pulse with an intensity having a magnitude and a duration, wherein the magnitude is as much as but less than three times a threshold value that would otherwise directly stimulate the heart muscle;

pacing a sequence of heart muscle cycles with an electronic pacing device wherein the pacing device is positioned on the patient at a distance from the heart muscle to detect a local electrical event with which to trigger a start time $t_0$ for a predetermined stimulation interval;

positioning an electrode/sensor in an epicardial vein adjacent the sympathetic nerve, wherein the sympathetic nerve is located on the epicardial surface over the left ventricle of the heart muscle;

engaging the pacing device and the electrode/sensor with a timer to establish an electrode activation at the start time $t_0$ for the stimulation interval;

stimulating the sympathetic nerve with at least one electrical pulse at a time $t_1$ for a release of norepinephrine during the absolute refractory period;

controlling the pre-programmed intensity of each pulse during the stimulating step to indirectly assist a subsequent natural stimulation of the heart muscle for improved contractions of the heart muscle after the absolute refractory period;

repeating the stimulating step during each successive heart function cycle.

* * * * *